United States Patent
Wilson et al.

(10) Patent No.: US 6,170,929 B1
(45) Date of Patent: Jan. 9, 2001

(54) AUTOMATED MEDICATION-DISPENSING CART

(76) Inventors: Ronald H. Wilson, 19108 Waxen Rd.; Michael A. Stoy, 19324 51st Avenue SE., both of Bothell, WA (US) 98012

( * ) Notice: Under 35 U.S.C. 154(b), the term of this patent shall be extended for 0 days.

(21) Appl. No.: 09/204,814

(22) Filed: Dec. 2, 1998

(51) Int. Cl.[7] .................................................. A47B 49/00
(52) U.S. Cl. ...................... 312/268; 700/243; 221/21; 221/76
(58) Field of Search .................................. 221/2, 21, 69, 221/76, 77, 117, 121, 122, 185; 700/243; 312/267, 268

(56) References Cited

U.S. PATENT DOCUMENTS

| | | | |
|---|---|---|---|
| 2,710,240 | * 6/1955 | Berg | 312/268 |
| 3,159,441 | * 12/1964 | Sikma | 312/268 |
| 4,779,938 | * 10/1988 | Johnston | 312/268 |
| 4,811,764 | 3/1989 | McLaughlin . | |
| 4,813,752 | * 3/1989 | Schindler | 312/268 |
| 4,847,764 | 7/1989 | Halvorson . | |
| 5,011,240 | 4/1991 | Kelley et al. . | |
| 5,014,875 | 5/1991 | McLaughlin et al. . | |
| 5,272,321 | * 12/1993 | Otsuka et al. | 221/7 |
| 5,314,243 | 5/1994 | McDonald et al. . | |
| 5,392,951 | 2/1995 | Gardner et al. . | |
| 5,431,299 | * 7/1995 | Brewer et al. | 221/76 |
| 5,438,523 | * 8/1995 | Humm et al. | 700/243 |
| 5,460,294 | 10/1995 | Williams . | |
| 5,820,237 | * 10/1998 | Robey | 312/268 |

FOREIGN PATENT DOCUMENTS

404086983 * 3/1992 (JP) .......................................... 221/2

* cited by examiner

Primary Examiner—H. Grant Skaggs
(74) Attorney, Agent, or Firm—Jensen & Puntigam, P.S.

(57) ABSTRACT

An automated medication-dispensing cart includes a closed cart housing and a plurality of medication-containing bins which extend for substantially the length of the cart and which are supported within the cart housing. The support structure includes two spaced sets of sprockets positioned at both ends of the cart and endless chains which extend around the sprockets, with one of the sprockets being motor-driven. The bins are connected at opposing ends thereof to the spaced chains. The movement of the bins is controlled such that the bins can be stopped at a preselected position within the cart, in the vicinity of the top front edge of the cart. A plurality of doors is located in the top of the cart, such that when one or more of the doors is opened, a preselected portion of the bin in the preselected position and the medications therein are exposed.

24 Claims, 6 Drawing Sheets

AUTOMATED MEDICATION-DISPENSING CART

TECHNICAL FIELD

This invention relates generally to medication carts, which are used in hospitals and nursing facilities to temporarily store and dispense medications, and more particularly concerns such a medication cart having a novel medication-dispensing system.

BACKGROUND OF THE INVENTION

Medication carts in general are well-known. Such carts generally comprise a body or housing which is supported on wheels such that the cart can be readily maneuvered throughout a hospital or similar facility. The cart housing will typically include a plurality of individual medication bins housed in one or more cassette containers. The bins are assigned to particular patients (patient-specific), or contain particular medications (drug-specific) not assigned to a particular patient. If the individual bins are assigned to patients, there will often be an inefficient use of space in the bin, since prescribed medications for many patients will not require the space of an entire bin. In other cases, large dosage forms or multiple-day patient medications can require more than one bin for a single patient.

Medication carts also typically will have large miscellaneous drawers for storage of containers of particular medications, such as aspirin, syrups, etc. Non-medication supplies are also kept in the miscellaneous drawers. In all cases, the nurse must find and then pick the correct amount of the correct medications and/or supplies within the bin. Inventory management is imprecise because the nurse may take too few or too many doses or misplace doses which are returned to the cart.

This lack of dosing and inventory management leads to medication dosing errors. In addition, there are errors in the manual dispensing of medications into the bins by the pharmacy, and there is no closed-loop monitoring control over medications in the cart, the pharmacy and/or the nursing stations.

Also, such medication carts are typically inconvenient to access. The cart may have locked doors which require keys or other controlled means of access. Further, when the doors are opened, the entire medication cart, including all of the bins, is often accessible, instead of just the desired patient's bin or particular medications. This allows "borrowing" of medications from another bin, mistakes and even theft. Access to the bins is also in many cases physically inconvenient because of the operator having to bend over or kneel to access desired bins and drawers.

Hence, it would be desirable to have a medication cart which is more efficient, easily accessible and more convenient to use. In addition, it would be helpful to be able to conveniently limit access to a single unit of use in one desired bin to prevent errors and theft.

DISCLOSURE OF THE INVENTION

Accordingly, the present invention is an automated medication-dispensing cart, comprising: a substantially closed cart housing; a plurality of medication-containing bins; means for supporting the individual bins within the cart housing; means for moving the bins within the cart in a controlled manner, such that a bin can be stopped at a preselected position in the vicinity of the top of the cart; and means for opening a door assembly from a closed position, the door assembly being located at the preselected location, exposing a selected portion of the bin when it is in the said preselected position.

BEST MODE FOR CARRYING OUT THE INVENTION

Figure 1:
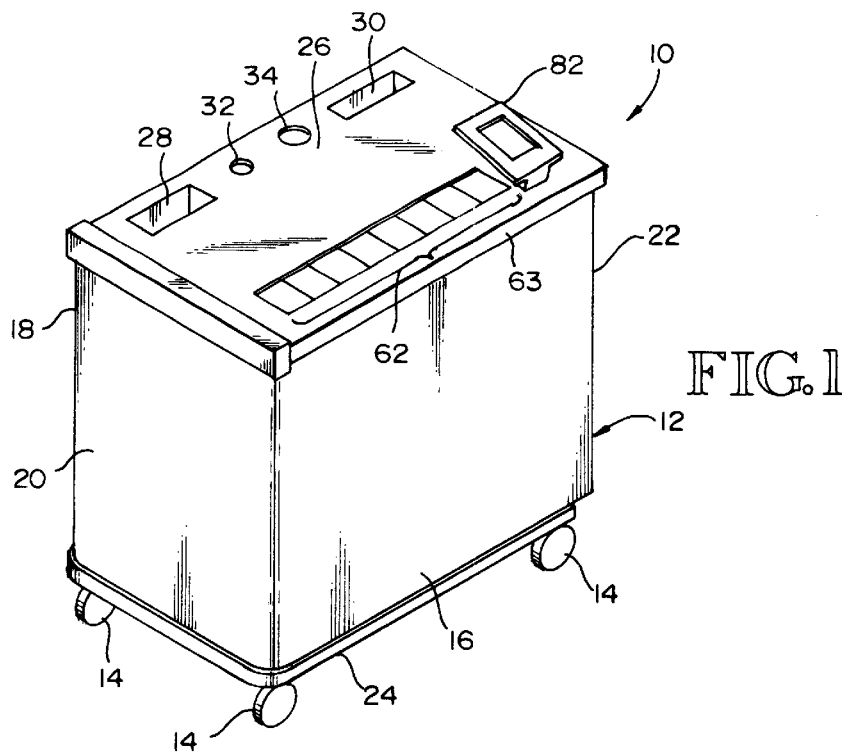
FIG. 1 is an isometric view showing the exterior of the medication cart of the present invention.

FIG. 1 shows the exterior of the medication cart of the present invention generally at 10. It includes a cart housing or body 12 supported by casters 14—14 at each bottom corner of the housing. Casters 14—14 permit the cart to be moved throughout the facility in which it is used. The cart body includes front and rear panels 16 and 18, two end panels 20 and 22, a base member 24 and a top member 26.

At the rear of the top member 26 are four spaced openings, each one of which accesses a container within the cart body. In the cart shown, opening 28 is for returned (unopened) medications and opening 30 is for trash, including used medication packaging. opening 32 is for sharps, such as needles, while opening 34 holds soufflé cups. All of the features are conventional for a medication cart. Other conventional features, including a night reading light, straw holder, water pitcher holder, etc. can be added to the cart if desired.

FIGS. 2–9 show the medication-dispensing system within the cart housing 12. Medications and other medical elements, such as syringes, IVs, etc., are contained in a plurality of medication bins 40. In the embodiment shown, there are approximately 22 bins which are contained within the cart housing, although this number can be varied depending upon the actual bin size, the physical arrangement of the dispensing system and the cart housing. Each bin is approximately 28 inches long, somewhat less than the overall length of the cart.

The bins 40 are generally in the form of a half-cylinder, with flattened sides and bottom, with a diameter of approximately four inches. Such a bin is shown in detail in FIG. 8. In an alternative arrangement, the bins could be rectangular. The bins can be provided with a cover assembly 41 which will maintain the medications in place as the bins are moved through the dispensing system, as described below, and as the bins are transported between facilities. The cover 41 can be manually or automatically controlled. The bins can be subdivided into smaller, individual segments or sections 43 by means of removable partitions 45 which are positioned at selected points along the length of each bin. The length of the individual sections in a particular bin is not necessarily fixed, but can be changed according to the needs of the user.

A single bin, instead of being assigned to just one patient or used for a single medication, can be used by more than one patient, depending upon the physical volume of the medications prescribed for those patients. Access to the bins, as explained more fully below, will be provided only to the sections of the bin necessary, i.e. those which contain the desired medications or medical elements. For particular patients, if necessary, an entire bin can be used, without any dividers. The section dividers or partitions 45 will typically be securely fastened, such as by screws or pins or the like, to prevent removal thereof, except to accomplish deliberate reconfiguration of the bins.

The bins are supported for movement within the housing by a support assembly. The support assembly includes two side supporting plates 42, 44 (FIG. 4) located at opposite ends of the cart. Supporting plates 42, 44 are approximately the same size as the end panels of the cart. Mounted to each supporting plate are a set of sprockets 46. In the embodiment shown, there are a total of five sprockets in each set mounted for rotation on each supporting plate. The sprockets are mounted in the vicinity of each corner of the supporting plates, with a fifth sprocket mounted approximately in the middle of each supporting plate. The sprockets on each plate, except for the one in the upper front corner thereof, are 45-teeth idler sprockets. The two remaining sprockets (one on each plate) are 54-teeth large chain drive sprockets 46a, 46b, respectively.

Endless chains 47, 48 extend around each set of sprockets, although other drive means, such as belts, could be used. Each bin is mounted at its respective ends thereof to the spaced chains via connecting pins or similar elements. Moving the chains will move the individual bins through a particular path of travel (serpentine in the embodiment shown) within the cart housing.

Figure 4:
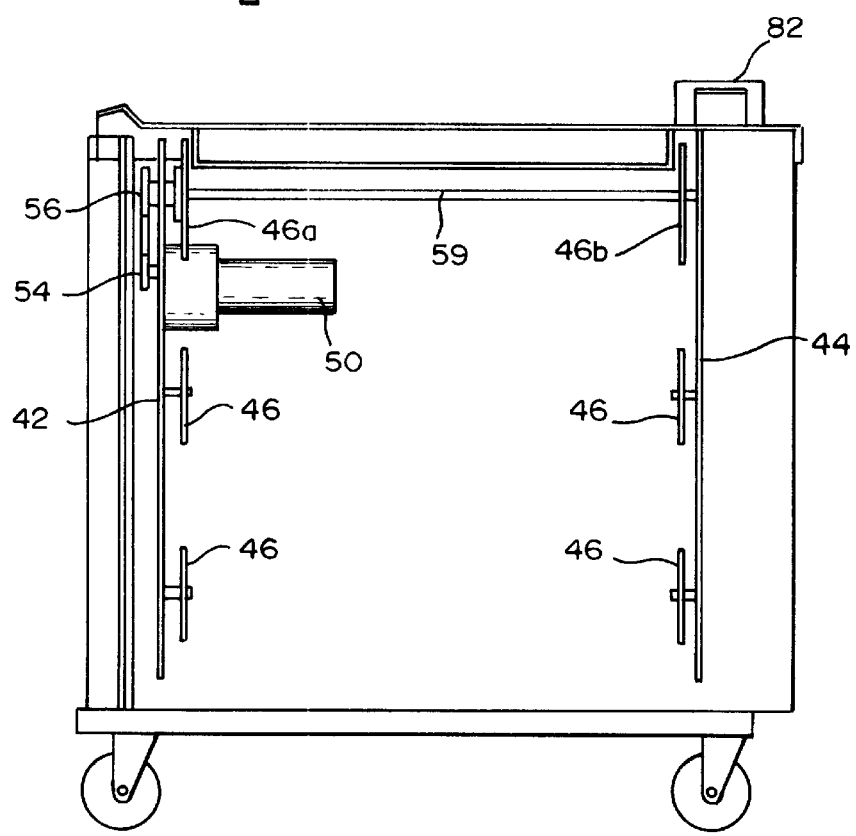
FIG. 4 is a front view of the medication cart of FIG. 2.

Driving the support assembly in the embodiment shown is a conventional drive motor 50, as shown most clearly in FIG. 4. Drive motor 50 drives a motor shaft on which is mounted at the distal end thereof a first motor drive sprocket 54. A drive chain 58 links the first motor drive sprocket 54 to a second motor drive sprocket 56 mounted on shaft 59, which extends the length of the cart and is mounted for rotation to both supporting plates 42, 44. The two large chain drive sprockets 46a, 46b are mounted on shaft 59.

Figure 2:
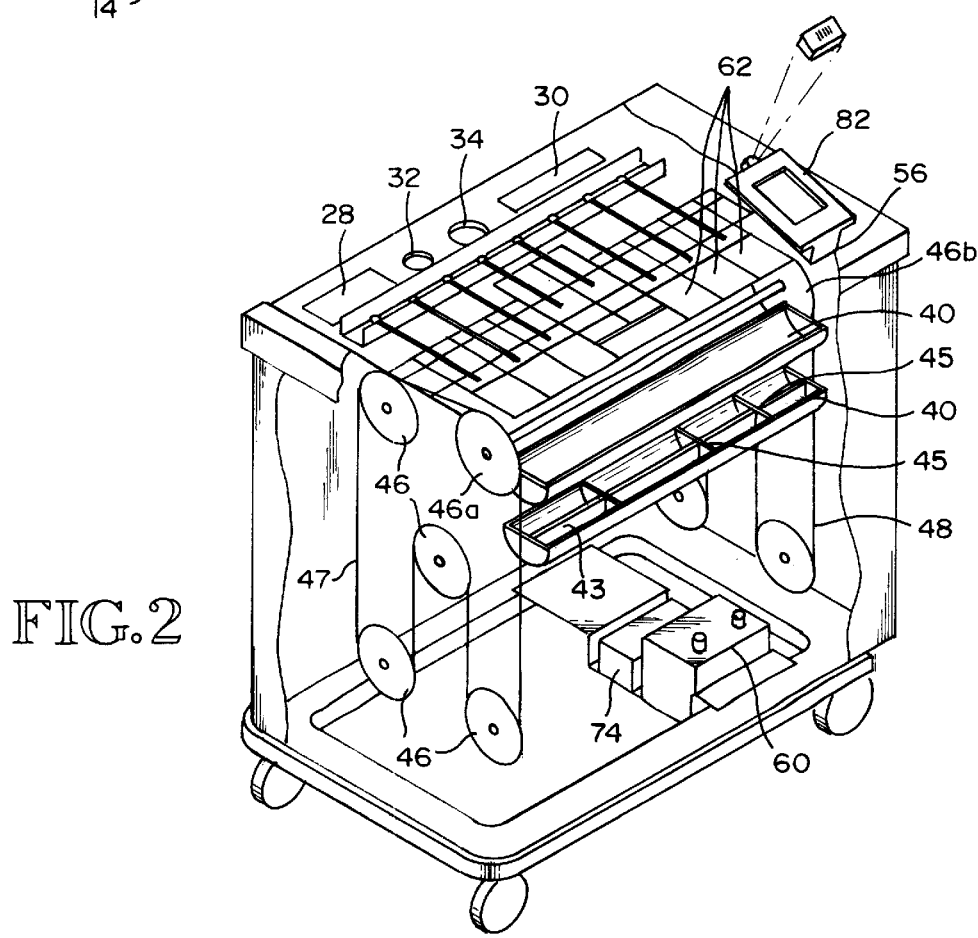
FIG. 2 is an isometric view showing generally the interior structural arrangement of the medication cart of FIG. 1.
Figure 3:
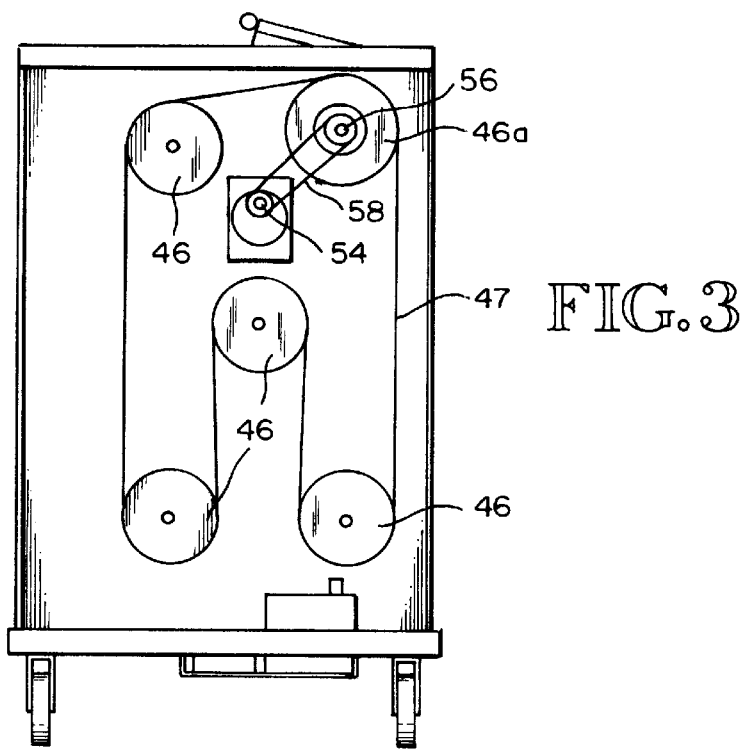
FIG. 3 is an end view of the medication cart of FIG. 2.

As shown in FIGS. 2 and 3, endless chains 47, 48 each follow a serpentine path within the cart housing around its set of sprockets, one in each set being a chain drive sprocket mounted on drive shaft 59. This structural arrangement permits a relatively large number of bins to be contained within the medication cart housing. Motor 50 is a reversible motor, so that the bins can move in both directions on the serpentine path. Motor 50 is powered by a rechargeable battery 60 in the embodiment shown, although other means of power can be utilized.

Top member 26 of the cart includes a large opening near the front edge thereof and a plurality of individual sliding doors 62 immediately below the opening, covering the opening. The doors extend along the length of the cart in the vicinity of the front (near) edge 63 thereof. Thus, when one or more doors open, the bin therebeneath within the housing is exposed. When the doors are closed, the opening is completely covered. One or more doors 62 exposes each section of a bin when opened. When a particular bin is configured to have a large section, sufficient numbers of doors can be opened to reveal the entire bin section at once.

The system can also be arranged to partially open one or more doors, to expose half of a particular section longitudinally, when the bin is configured that way. The doors 62 are normally closed and locked. In the embodiment shown, each door is approximately 4 inches wide and is mounted to slide laterally (from front to rear) just beneath the opening in the top member of the cart, from a closed position in which the free edge 65 of the door abuts against the near edge of the opening located at the near top edge of the cart.

Figure 5:
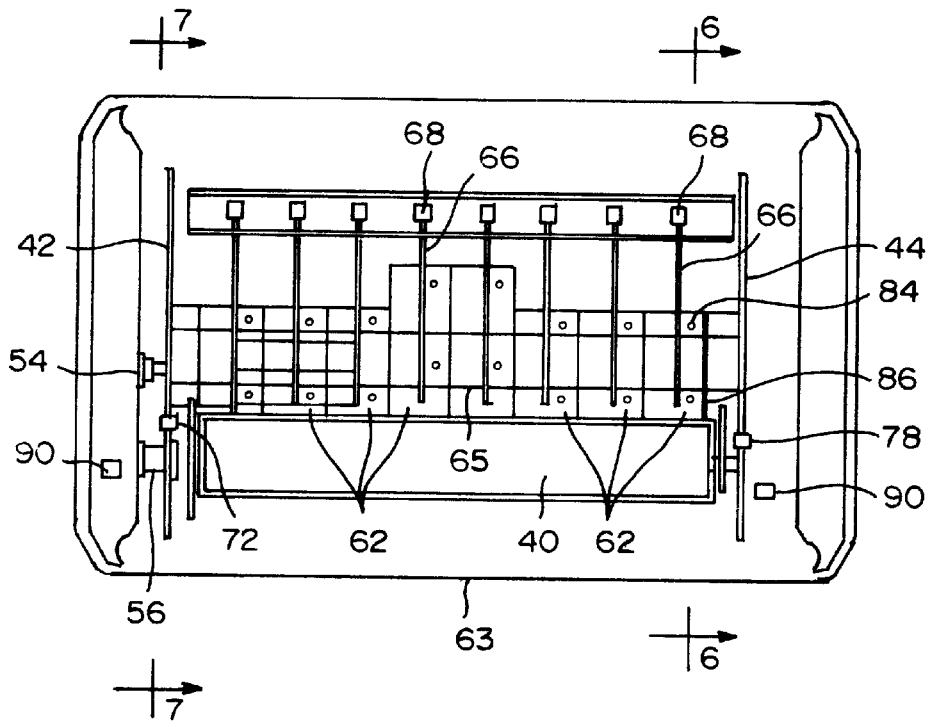
FIG. 5 is a top view of the medication cart of FIG. 2.
Figure 9:
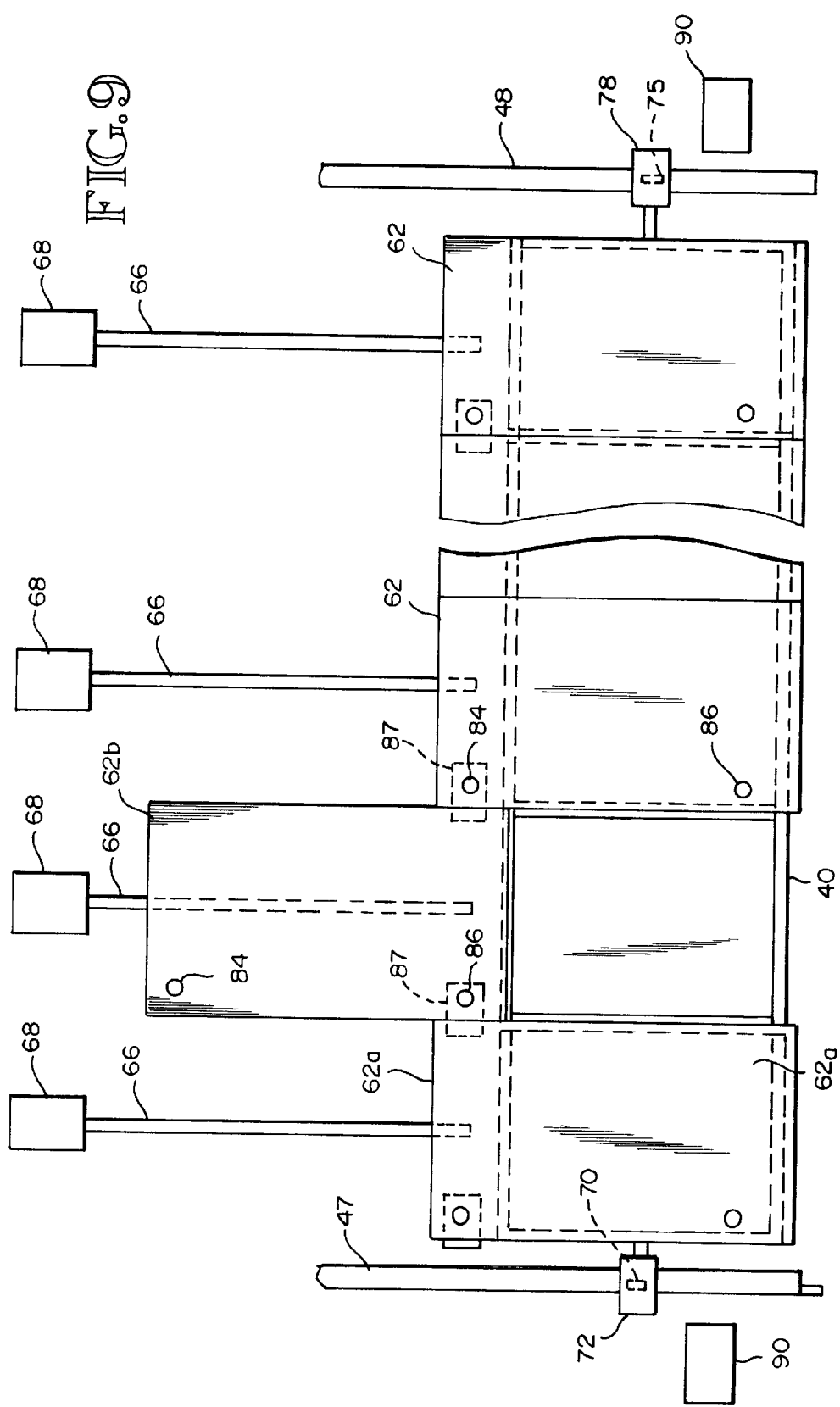
FIG. 9 is a top plan view of the doors at the top of the medication cart, with associated sensors.

Each of the doors 62 will have associated therewith an actuator, such as a motor/lead screw arrangement, a rotary servo and rod or pneumatic cylinders. The embodiment shown illustrates an actuator rod 66 and its associated motor 68 as shown in FIGS. 5 and 9. When the motor turns in one direction, the door opens (door 62b); when it turns in the other direction, the door closes (door 62a). The opening/closing of the doors is controlled by a hand-held computer via an IR or RF unit or by a computer built into the cart. The individual doors extend along substantially the entire length of the cart, and when medications are not being dispensed, the doors are closed and locked. An alternative actuator arrangement could include a top door to protect against spills with a pawl link to bin doors. The correct pawl links will be actuated for each selected bin. Opening of the top door will then draw back the particular bin doors which are to be opened.

Figure 7:
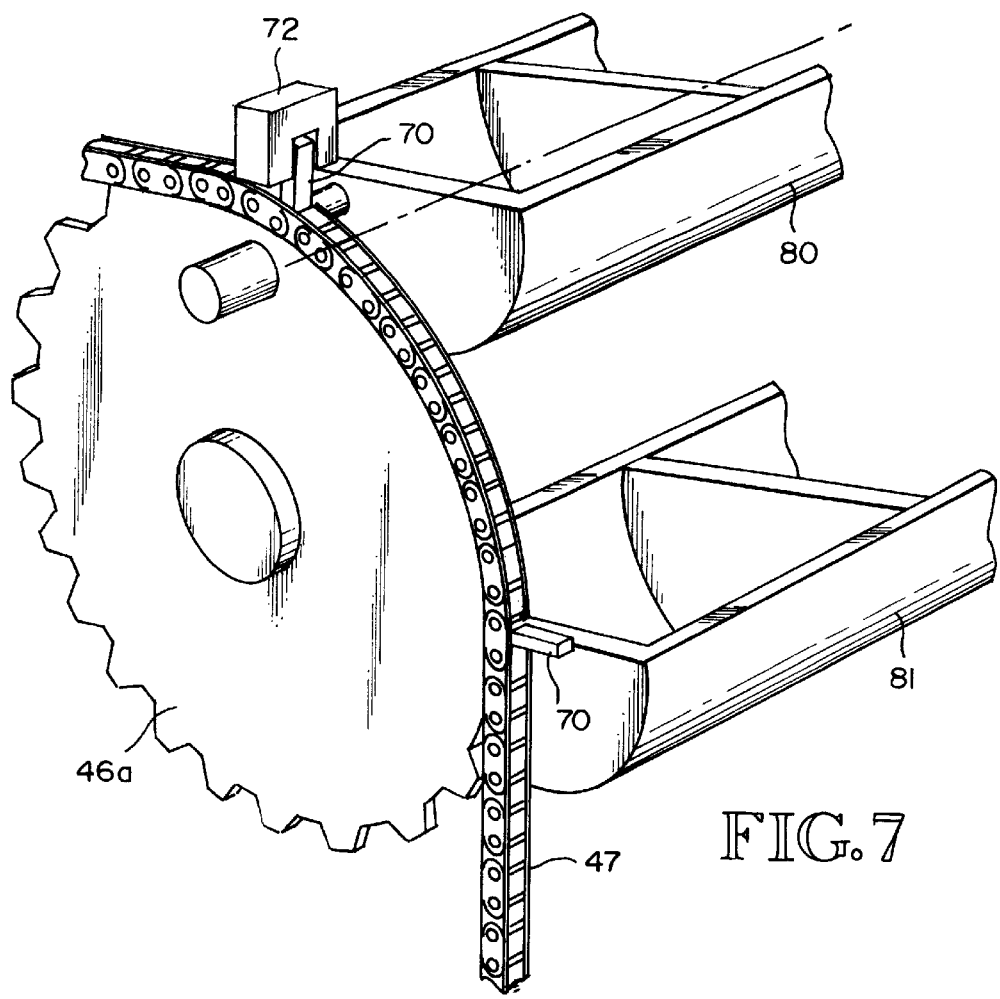
FIG. 7 is a partial cross-section view of FIG. 5 taken along lines 7—7.
Figure 8:
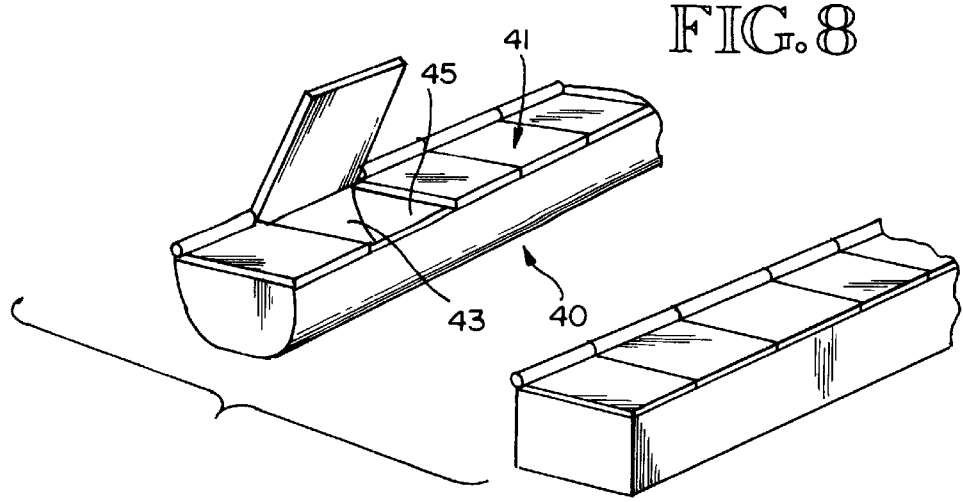
FIG. 8 is a perspective view of one bin used in the embodiment of FIGS. 1–7.

At one end of each of the bins, attached to the chain at that end, are first sensor tabs 70 (FIGS. 5 and 7). As the drive motor 50 is actuated, moving the series of bins supported by the spaced chains 47, 48 through a path of travel, the first sensor tabs 70 pass by a first optical sensor 72 located at the front corner of the cart, adjacent the chain 47. The sensor 72 could be a proximity switch, reed switch or other sensing element. This tab/sensor arrangement identifies the position of each bin (80 and 81 in FIG. 7) when it reaches the top front (near) edge 63 of the cart. This information is transmitted to an on-board microprocessor 74.

Figure 6:
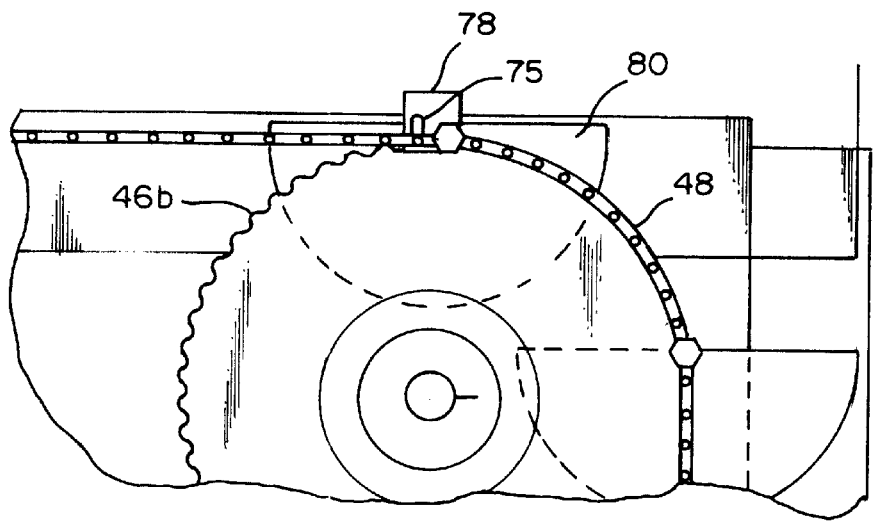
FIG. 6 is a partial cross-section view of FIG. 5 taken along the lines 6—6, showing the "home" sensor tab and sensor.

A second sensor tab 75 is located at the other end of just one of the bins, referred to as the "home" bin 80 (FIGS. 5 and 6). Another optical sensor 78 is located near the opposite front corner of the cart to identify tab 75. The arrangement of sensor tabs 70 and sensor 72 is shown most clearly in FIG. 7, which also shows drive sprocket 46a, chain 47 and a bin 80, which is the home bin in the embodiment shown. Sensor tab 75 and sensor 78 at the other end of the "home" bin 80 are shown most clearly in FIG. 6, with drive sprocket 46b and chain 48.

In typical operation, when cart 10 is actuated, motor 50 is turned on to move the bins until home bin 80 is in the home position, as determined by sensor tab 75 and sensor 78. Once home bin 80 is in the home position at the top front of the cart, as shown in FIGS. 6 and 7, the position of all the other bins relative thereto can be easily determined by the on-board microprocessor 74.

The operation of the cart is commanded by a small operator's computer 82, which is either mounted on the top of the cart or is a hand-held unit. The hand-held operator's computer communicates with the on-board microprocessor 74 by means of an IR (infrared) link, RF (radio frequency) link or with computer hard wiring connections. The on-board microprocessor 74 controls motor 50 and the actuators 66 for doors 62, so that when a particular patient is identified through the operator's computer 82, motor 50 will be actuated to position the correct bin at the dispensing location at the upper front of the cart and the correct doors will be opened to expose the desired section of the bin immediately below. Use of a radio link would permit the nurse to control the cart when out of the room. Also, the cart can be made to work without an operator's computer. An entry device for receiving the patient's name and ID number is used, which is the minimum information necessary to operate the cart.

Two magnets 84 and 86 are secured to the top of each door. A reed switch 87, sensor or similar device is fixedly mounted below each door near a rear edge of the door (when the door is closed, such as door 62a in FIG. 9). The magnets and sensor are arranged such that when the door is fully open, one of the magnets (84 in FIG. 9) is over sensor 87, and when the door is fully closed, the other magnet (86 in FIG. 9) is over sensor 87. The sensor 87 is electrically connected to the on-board microprocessor 74, so that the microprocessor knows the location of all the doors at all times. If the microprocessor 74 commands one or more door motors to open or close its associated door, and that door does not respond appropriately, an error message is sent to the operator's computer 82 by the microprocessor. Messages can also be sent for errors with the other sensors which detect bin movement.

In operation of the cart, the appropriate number of sections of a particular bin are assigned to a given patient to receive medications or other medical elements, such as IVs, syringes, bandages, etc. As indicated above, the sections can be easily configured to accommodate the needs of each individual patient. The section sizes can be configured to accommodate a variety of medications and other medical elements. As indicated above, the patient is assigned only as much space in a particular bin as is necessary for his/her medications and other medical elements, such as syringes, IVs, etc. This arrangement makes maximum use of available bin space, thereby making the overall bin arrangement more efficient, i.e. the cart is able to accommodate more patients with the same number of bins.

When a particular patient is to be given his/her medications, the nurse will initiate action via the operator's computer/scanner 82. Once the nurse is logged on, the operator's computer, through an RF link with the hospital's central pharmacy computer, will display a list of patients for the location in the health facility serviced by the cart. The nurse will then select a particular patient, from a list of patient names displayed by the computer, who is to be given medication. That particular patient's medication information will then be displayed on the operator's computer. The medication information for the particular patient is stored in the operator's computer and is updated prior to display by contact with the hospital's central pharmacy computer.

The on-board microprocessor identifies from its memory the particular bin and the sections thereof which correspond to the selected patient and will signal the drive motor 50 to move the medication-dispensing system so that the correct bin is in the "home" position at the top front edge 63 of the cart. Once the proper bin has been located and is in the home position, the actuators 66 for the appropriate doors 62 are operated, opening the correct doors and exposing the sections in the bin containing the patient's medications and/or other medical elements. These control functions performed by the microprocessor are routine, and, accordingly, the control software is not disclosed in detail herein. The nurse then removes the medications from the bin. If the bin has a cover on it, the cover is first opened, either by hand or automatic actuation, to reveal the contents of the bin.

The individual sections of a bin could contain individual starter, regular dose or on-demand medications. The nurse could be provided access to a section with a medication prescribed for the particular patient at that time. However, not all sectors are patient-specific. Some may be medication-specific.

Typically, but not necessarily, the medications will be bar-coded. When the medications are removed, the nurse will scan the medications with the operator's computer/scanner, and the computer will cross-check the medications against the patient's medication information in the operator's computer. The patient's identification number (bar code) is then verified by the nurse by scanning the patient's wrist band. The verified medications will then be administered by the nurse.

When the medications have been administered, the nurse takes the packaging for such medications and places it in the waste bin opening 30. There is also an opening, as indicated above, for unopened medications, as well as openings for sharps and soufflé cups.

The bins can be also filled automatically, although this is not necessary to the present invention. The bins can be filled by hand. The cart containing the bins to be filled is brought by a courier beneath an automated loading device (robot) attached to a pharmacy computer. The individual bins on the cart will be exposed, with the correct medications being selected automatically by the robot from stores thereof and dispensed into the correct bins (or sections thereof). When a medication or other medical element after loading extends above the top edge of the bin, an over-height emitter-sensor 90 located on the cart will alert the bin-filling robot to the presence of an over-height medication. The operator can then open the filling funnel and pat down the medication. When all of the bins have been filled, the cart is then moved by a courier back up to the area where it is used.

One of the advantages of the arrangement shown herein is that the apparatus can in one arrangement be very sophisticated, with fully automatic loading and real time communication links between the operator's computer (usually hand-held), the cart itself, and the facility central computer. In such a case, all of the medications can be bar-coded for accurate tracking and control.

Alternatively, in another arrangement, the apparatus can be relatively simple, with the bins loaded by hand, with no bar coding of the individual medications or other medical elements, and with the particular bin section assignments for a particular patient being entered at the cart itself, without an operator's computer. However, control signals will in all cases be provided to the on-board microprocessor, which will both control movement of the proper bin to the "home" position and then open the proper doors to expose the desired medications to the nurse. The on-board microprocessor, which normally controls the hardware movement, could serve the function of the hand-held or cart-top computer as well, if it had the required capability.

Hence, a medication cart has been disclosed which solves many of the problems and concerns with respect to prior carts. The arrangement provides access to only the required bins/segments of the bins for a particular patient, and moves the correct bin to a home position which is at the top front edge of the cart. This eliminates any bending or stooping by the nursing staff, and results in a very efficient and convenient medication cart arrangement. FIGS. 1–9 show a particular bin arrangement and movement within the cart. Alternative arrangements are certainly possible, however, within the context of the present invention. A few such arrangements are discussed below.

Figure 10:
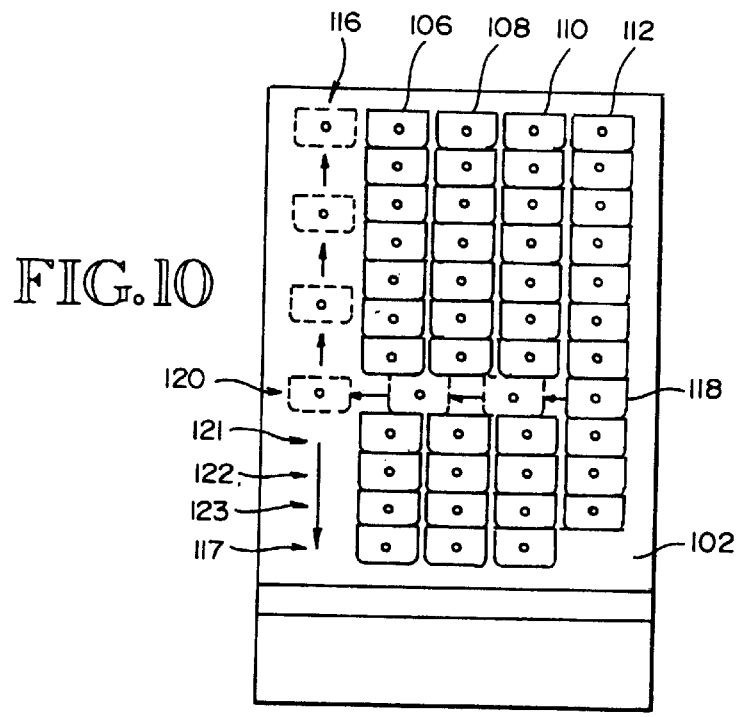
FIG. 10 is an elevational view of an alternative bin arrangement in a medication cart.

FIG. 10 shows an alternative arrangement or stack of multiple bins in a cart, within the same general concept of the embodiment of FIGS. 1–9. In this arrangement, shown as an end view of the cart, there are four vertical columns or stacks of bins which extend from one end 102 of the cart to the other end thereof, with each of the four columns 106, 108, 110 and 112, containing 12 individual bins. The arrangement has 11 horizontal rows of 4 bins and 1 empty row 117 with no bins. There is also a vertical open space or column 116 to the left of column 106 which permits bins to move vertically for the height of the cart.

When a particular bin is desired from the arrangement of FIG. 10, the bins to the left of the desired bin in the particular row containing the desired bin and the bins located below those bins in the particular row are moved down to the empty row 117, except for the column containing the desired bin. The desired bin is then moved to the left out into the open column 116 and then moved up to the top of the stack, where it is positioned so that it can be accessed by a nurse or other operator through the door assembly in the top of the cart. In FIG. 10, bin 118 is shown being moved out in dotted lines. The bins in columns 106, 108 and 110, rows 120–123, are all first moved down one row. Bin 118 is thus free to move out.

The vacant row 117 thus permits the bins in the rows below the desired row to be moved down conveniently and as necessary, so that a desired bin can be moved to the open column and then upwardly to the top of the stack. The advantages of this system are a relatively high bin density, with fast access, and without the necessity of covers for the individual bins. However, the mechanism for locating and retrieving a particular bin is relatively complex. Further, the bins require a lot of individual movement and the serial access could result in reliability problems.

Figure 11:
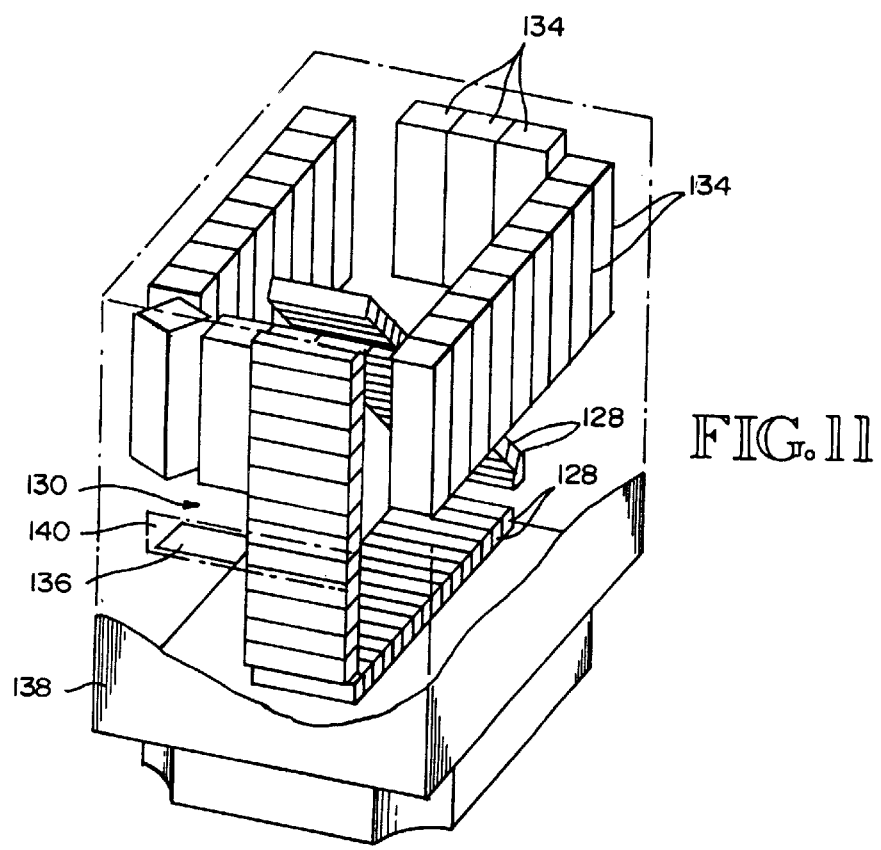
FIG. 11 is a perspective view of another bin arrangement for a medication cart.

FIG. 11 shows another alternative bin arrangement. The individual medication bins 128 are located on an endless conveyor track 130, the bins being supported horizontally and with the endless track forming a right-angled triangle arrangement. Access to the individual bins 128 is provided at the top of the cart through an opening in the top surface thereof (not shown). The individual horizontally oriented bins require covers, since they turn upside down during part of the time that they are moving along the path of travel. When a particular bin is selected, the conveyor 130 is moved until the desired bin is at the uppermost portion of the triangular path, directly beneath a door in the top of the cart, which provides access to the bin. The door is opened and the nurse can then lift the door on the desired bin and remove the medications.

Arranged around the interior periphery of the cart housing are a series of receptacles 134. Each receptacle is large enough to contain an IV or similar article. The receptacles 134 are arranged to move horizontally around the periphery of the housing, by means of a chain drive or other mechanism. The drive mechanism stops the desired receptacle immediately above a tray or like element 136 at one end 138 of the cart housing. The receptacle 134 is then opened so that the IV or other article drops into tray 136. Access to tray 136 is provided by a door 140, shown in dotted lines in FIG. 11.

In this embodiment, the drive mechanism and the basic arrangement of the bins are relatively simple. Also, the arrangement can be conveniently changed to accommodate a different number of receptacles and bin elements. This arrangement, however, does limit the number of bins which can be positioned within a housing, and provides only a serial access to the bins, as opposed to more desirable random access. Further, this arrangement will require that the medication bins have lids, since during a portion of the bin travel they are upside down.

Although a preferred embodiment and other arrangements of the invention have been disclosed herein for illustration, it should be understood that further changes, modifications and substitutions may be incorporated in such embodiment without departing from the spirit of the invention, which is defined by the claims as follows:

What is claimed is:

1. An automated medications-dispensing cart for use by a health care professional in dispensing medications to a plurality of patients, comprising:

a substantially closed portable cart housing, the cart housing including a flat top working surface for the nurse/health practitioner;

a plurality of medication-containing bins;

means for supporting the individual bins within the cart housing;

means for moving the bins within the cart housing in a controlled manner, such that a bin can be stopped at a preselected position in the vicinity of the top front edge of the cart housing;

means for opening a door assembly from a normally closed position and then returning it to its closed position, the door assembly being located at the preselected position, exposing a selected portion of the bin when it is in said preselected position; and an onboard microprocessor for controlling the movement of said moving means and said opening means, the microprocessor operating in response to a control signal from a computer source thereof, which is located external to the microprocessor.

2. An apparatus of claim 1, wherein the bins are subdividable into sections.

3. An apparatus of claim 2, wherein the bins are subdividable both laterally and longitudinally.

4. An apparatus of claim 1, wherein said preselected position is at the top front edge of the cart and extends longitudinally along the cart.

5. An apparatus of claim 1, wherein said preselected position is at the top of the cart near one end thereof and extends laterally of the cart.

6. An apparatus of claim 1, wherein said bins extend for substantially the length of the cart.

7. An apparatus of claim 1, wherein said bins extend for approximately the width of the cart.

8. An apparatus of claim 1, wherein the bins are elongated and are divided into sections by bin partitions.

9. An apparatus of claim 1, including means for supporting the bins at opposing ends thereof.

10. An apparatus of claim 1, wherein the bins are approximately in the form of elongated half-cylinders, with flattened side and bottom portions.

11. An apparatus of claim 1, wherein the bins are rectangular.

12. An apparatus of claim 1, including a cover assembly for covering each bin.

13. An apparatus of claim 1, including means for monitoring the position of the bins as they are being moved, so that a selected bin can be reliably located at said preselected position.

14. An apparatus of claim 1, wherein the door assembly includes a plurality of individually controlled doors in the top of the cart movable between a closed position and an open position, and wherein the opening means includes means for opening selected doors to expose a particular portion of said bin containing medications for a particular patient.

15. An apparatus of claim 14, wherein the moving means includes a motor and actuator assembly responsive to a control signal for opening selected doors.

16. An apparatus of claim 14, including sensor means to determine whether the individual doors are open or closed.

17. An apparatus of claim 1, wherein in operation, the bins move along an endless loop path of travel, wherein the moving means includes two pluralities of supporting sprockets and an endless drive member which extends around sprockets positioned at opposing ends of the cart and further includes connectors connecting the ends of each bin to the chains.

18. An apparatus of claim 1, wherein the bins move along a path of travel between first and second separated positions.

19. An apparatus of claim 1, wherein the control signal is generated by a computer mounted on the cart.

20. An apparatus of claim 1, wherein the control signal is generated by a hand-held computed by an operator to control the operation of the cart in response to entry of a particular patient's identity by an operator.

21. An apparatus of claim 1, including means for locking the door assembly in a closed position.

22. An apparatus of claim 1, wherein the medications are bar-coded and wherein the apparatus includes scanning means for reading the bar code on the medications.

23. An automated medications-dispensing cart, comprising:

a substantially closed cart housing;

a plurality of medication-containing bins;

means for supporting individual bins within the cart housing;

means for moving the bins within the cart housing in a controlled manner, such that a bin can be stopped at a preselected position in the vicinity of the top front edge of the cart housing;

means for opening a door assembly from a normally closed position, the door assembly being located at the preselected position, exposing a selected portion of the bin when it is in the preselected position; and an indexing system for determining the position of each bin within the cart relative to the preselected position, wherein the indexing system includes one tab element positioned on a selected bin and one sensor located at the preselected position, so that the selected bin can be located in the preselected position, and wherein the indexing system further includes a bin position determining assembly for ascertaining the position of each bin relative to the preselected position.

24. An automated medication-dispensing cart, comprising:

a substantially closed cart housing;

a plurality of medication-containing bins;

means for supporting the individual bins within the cart housing;

means for moving the bins within the cart housing in a controlled manner, such that a bin can be stopped at a preselected position in the vicinity of the top front edge of the cart housing;

means for opening a door assembly from a normally closed position, the door assembly being located at the preselected position, exposing a selected portion of the bin when it is in the preselected position; and sensor means to determine the presence of any medications which extend above an upper edge of the bin.

* * * * *